(12) United States Patent
Mogg

(10) Patent No.: US 9,433,754 B2
(45) Date of Patent: Sep. 6, 2016

(54) CATHETER CLAMP

(75) Inventor: Alan David Mogg, Ferndown (GB)

(73) Assignee: GOMA MEDICAL LIMITED, Ferndown (GB)

( * ) Notice: Subject to any disclaimer, the term of this patent is extended or adjusted under 35 U.S.C. 154(b) by 589 days.

(21) Appl. No.: 13/814,785

(22) PCT Filed: Aug. 5, 2011

(86) PCT No.: PCT/GB2011/051489
§ 371 (c)(1),
(2), (4) Date: Feb. 7, 2013

(87) PCT Pub. No.: WO2012/020246
PCT Pub. Date: Feb. 16, 2012

(65) Prior Publication Data
US 2013/0131600 A1 May 23, 2013

(30) Foreign Application Priority Data
Aug. 11, 2010 (GB) .................................. 1013490.6

(51) Int. Cl.
*A61M 5/32* (2006.01)
*A61M 25/02* (2006.01)
(52) U.S. Cl.
CPC ........ *A61M 25/02* (2013.01); *A61M 2025/024* (2013.01); *A61M 2025/0246* (2013.01)
(58) Field of Classification Search
CPC .............. A61M 2025/024; A61M 2025/0246; A61M 25/02
See application file for complete search history.

(56) References Cited

U.S. PATENT DOCUMENTS

| 4,397,647 | A | 8/1983 | Gordon |
| 5,690,616 | A | 11/1997 | Mogg |
| 6,500,154 | B1 | 12/2002 | Hakky et al. |
| 6,582,403 | B1 | 6/2003 | Bierman et al. |
| 2005/0192539 | A1 | 9/2005 | Bierman et al. |
| 2006/0058738 | A1 | 3/2006 | Ponzi et al. |
| 2006/0135944 | A1 | 6/2006 | Bierman |
| 2006/0276752 | A1 | 12/2006 | Bierman et al. |

FOREIGN PATENT DOCUMENTS

| EP | 1457227 A2 | 9/2004 |
| EP | 1537889 A2 | 6/2005 |
| GB | 2344054 A | 5/2000 |
| WO | 9116939 A1 | 11/1991 |

(Continued)

OTHER PUBLICATIONS

Search Report for GB Patent Application No. GB1013490.6, searched Oct. 25, 2010 (2 pages).

(Continued)

*Primary Examiner* — Rebecca E Eisenberg
(74) *Attorney, Agent, or Firm* — Tillman Wright, PLLC; James D. Wright; David R. Higgins

(57) ABSTRACT

A catheter clamp (1) comprising a base (2) and a pivotable cover (3), the cover arranged to be capable of adopting an open condition and a clamped condition, the clamp further comprising a resiliently biased displaceable latch (12) to releasably retain the cover in the clamped condition, wherein the latch displaceable on and relative to a support surface (11) which supports the latch, so as to release the cover from the clamped condition.

20 Claims, 6 Drawing Sheets

(56) References Cited

FOREIGN PATENT DOCUMENTS

| WO | 03068304 A1 | 8/2003 |
|---|---|---|
| WO | 2008151047 A1 | 12/2008 |
| WO | 2010002393 A1 | 1/2010 |
| WO | 2012020246 A1 | 2/2012 |

OTHER PUBLICATIONS

International Search Report of the International Search Authority in GOMA Medical Limited, et al., International Patent Application Serial No. PCT/GB2011/051489, dated Nov. 4, 2011 (4 pages).
International Preliminary Report and Written Opinion of the International Search Authority in GOMA Medical Limited, et al., International Patent Application No. PCT/GB2011/051489, dated Feb. 21, 2013. (4 pages).

CATHETER CLAMP

CROSS REFERENCE TO RELATED APPLICATIONS

This application is the U.S. national stage application under 35 U.S.C. §371 of International Application No. PCT/GB2011/051489, filed Aug. 5, 2011 and designating the U.S., which published as WO 2012/020246 A1 on Feb. 16, 2012, and which claims the benefit of United Kingdom Patent Application No. GB1013490.6, filed Aug. 11, 2010. Each of the foregoing patent applications and patent application publications is expressly incorporated by reference herein in its entirety.

TECHNICAL FIELD

The present invention relates to catheter clamps.

BACKGROUND

We have realised that there are various shortcomings in the function and efficiency of known methods of securing a cover of a catheter clamp in a clamping condition.

Broadly, known catheter clamps comprise two (plastic) components, a base and a cover/lid, hinged together such that when in an open condition, a catheter can be fed through the base and the base adhesively attached to a patient's skin around an insertion site in the skin. The cover is manually pivotable to grip the catheter and a retaining clip arrangement is operative to retain the cover in a clamped condition.

The retaining clip arrangement typically comprises two lugs which form a resilient part of the cover. As the cover approaches the clamped condition, the lugs are deflected by aperture-defining surfaces in the base. When the lugs have passed through the apertures, the lugs spring back and locate under the edges of the apertures. To release the retaining clip arrangement, the cover is lifted away from the base forcing the lugs out of the apertures.

One known catheter clamp comprises a feature whereby when in the clamped position co-operative faces on the cover and the base are forced together and held by a retaining clip arrangement to form a barrier to the ingress of infectious material. Also, the force required to compress the catheter into a close-fitting pathway of the base is held by the retaining clip. Both of those forces act against the retaining force of the clip, reducing the force required to release the clip.

In practice this undesirable balance of forces is difficult to maintain. Small dimensional variations in the plastic components, such as the size and position of pivot pins, pivot pin locations, co-operative faces of the cover and the base, as well as co-operative features of the clip, can build up and cause significant variation in the retain/release force. Also, the characteristics of the design means that a small variation in mould quality, such as the amount of rounding on the aperture edge and/or on the lugs, as well as flash from the moulding process inhibiting the amount of clip engagement, will cause further variation in the retain/release force. Furthermore, as the catheter clamp has to secure catheters from different manufacturers, variability in the diameters and compression strength of those catheters will also contribute to inconsistency in the retain/release force of the clip.

The sensitivity of the retaining force reduces the effectiveness of the catheter clamp. When the retaining force is low, the grip on the catheter is reduced. Also, a low retaining force reduces the force between co-opting faces and reduces the effectiveness of the bacteriological barrier. Furthermore, a low retaining force increases the risk of accidental release. However, when the retaining force is too strong then it is difficult to release the cover.

Because the clamp is released by forcing the cover away from the base, it is necessary to use two hands with one finger of one hand lifting the cover, whilst a finger from the other hand restrains the base from pulling away from the patient's skin. Because the clamps are small this can be an awkward operation.

Furthermore, because of the release method, it is necessary to provide a feature by which the cover can be lifted, and it is then susceptible to be accidentally caught in bedclothes, for example, which can cause the clamp to become released from the clamped condition.

The cover comprises two separate lugs spaced to each side of the catheter, and set apart at a distance to provide an even pressure on the co-operative sealing faces. However, in operation the cover can twist as the force is applied to operate the clamp and so only a single part of the clip is engaged, thus reducing the effectiveness of catheter clamping. This partial engagement would not be obvious to the user. Failure to fully engage both sides of the clip can reduce the grip on the catheter by up to fifty percent and cause the co-operative sealing faces not to come together.

We seek to provide an improved catheter clamp.

SUMMARY

According to one aspect of the invention there is provided a catheter clamp comprising a base and a pivotable cover, the cover arranged to be capable of adopting an open condition and a clamped condition, the clamp further comprising a resiliently biased displaceable latch to releasably retain the cover in the clamped condition, wherein the latch displaceable on and relative to a support surface which supports the latch, so as to release the cover from the clamped condition In one embodiment of the invention apertures which receive and retain lugs of the cover are provided in a spring-loaded slidable component entrapped within the base, such that in operation the lugs on the cover force the sliding component to one side against the force of a spring, allowing the lugs to pass through the apertures, the spring then causing the sliding component to return to its initial position and retain the lugs.

BRIEF DESCRIPTION OF THE DRAWINGS

Various embodiments of the invention will now be described, by way of example only, with reference to the following drawings in which.

DETAILED DESCRIPTION

Figure 1:
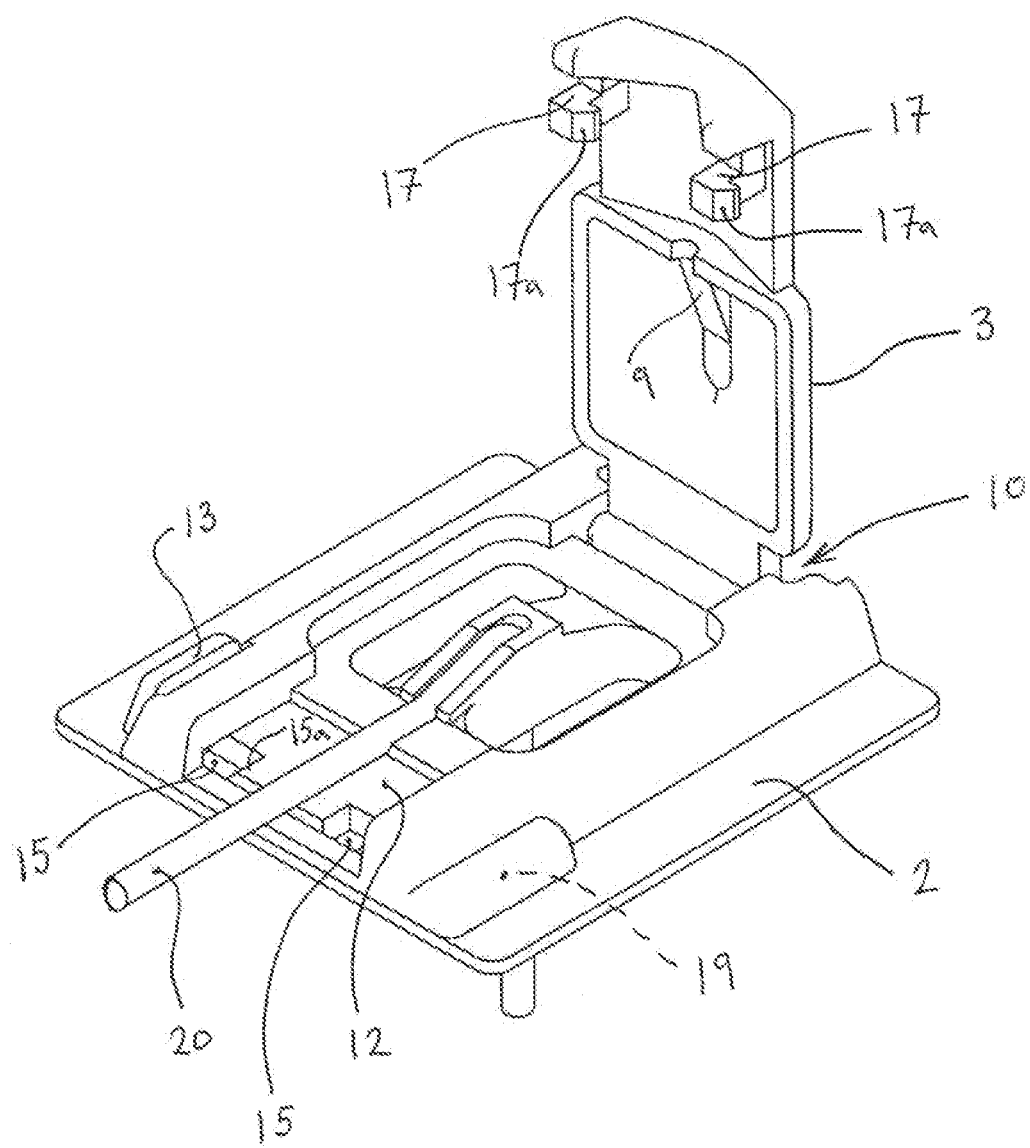
FIG. 1 is a perspective view of a catheter clamp in an open condition.
Figure 2:
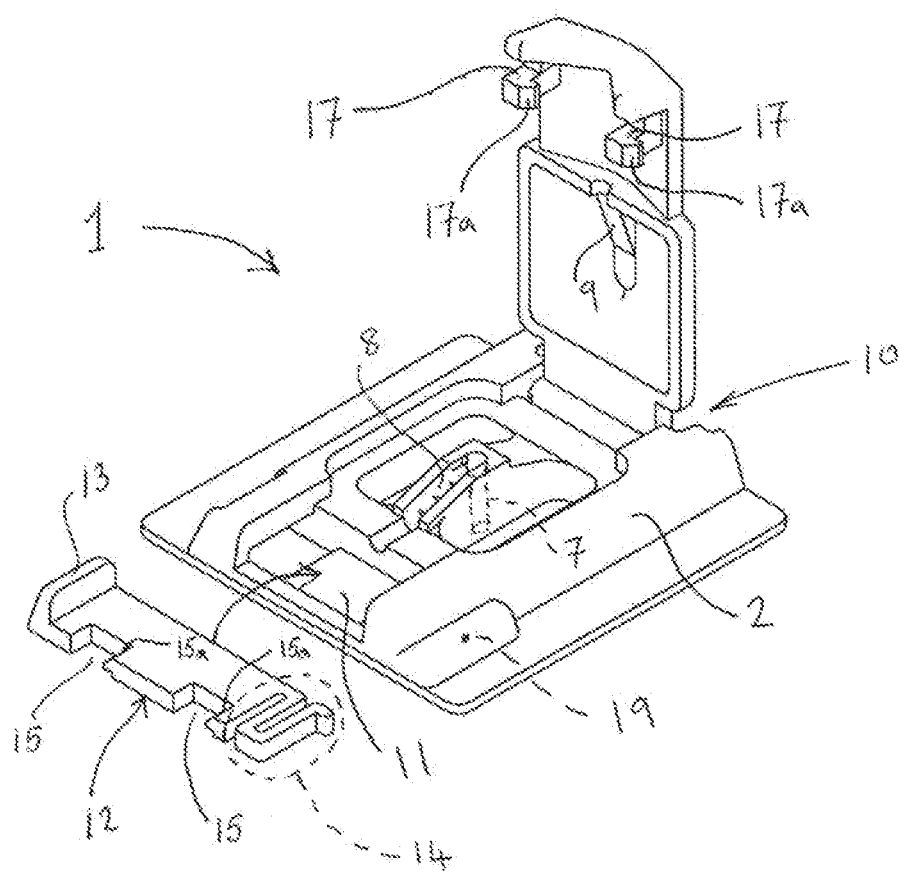
FIG. 2 is a perspective view of a catheter clamp in which a latch is shown as separate therefrom.

Reference is initially made to FIGS. 1 and 2 which show a catheter clamp 1 in an open condition. The catheter clamp 1 comprises a base 2 and a cover 3, the cover 3 being pivotably mounted at 10 to the base 2. The catheter clamp 1 is arranged to receive a catheter 20 in a vertical through-hole/bore 7 and in an open channel 8, the channel 8 being in communication with the through-hole 7. The channel 8 comprises an inclined portion and a (lower) horizontal portion. The through-hole 7 and the channel 8 are of substantially the external diameter of the catheter and form a close-fitting pathway for the catheter. On closure of the cover 3 to a clamped condition, an underlying portion 9 of the cover 3 urges the catheter into the channel 8 and causes the catheter to deform within the channel without any significant reduction in the cross-sectional area available for fluid to flow through the catheter. This controlled deformation of the catheter advantageously allows the catheter to be firmly gripped.

The cover 3 comprises, towards the free end thereof, two spaced-apart retainer formations/lugs 17, each essentially in the form of a hook. Each retainer formation depends from the cover and the hooked end portions of each are co-directional.

The catheter clamp 1 further comprises a latch 12 which is slidably mounted within the base 2. The latch 12 is essentially of elongate form and comprises an upstanding release portion 13, at a distal end thereof, a spring formation 14 at an opposite distal end, and two apertures 15 provided intermediately thereof. The latch 12 arranged for slidable movement parallel to the doubled-headed arrow shown in FIG. 1. The latch 12 is supported on a surface 11 and is displaceable on and relative to said surface.

When mounted in the base 2, the spring formation 14 bears against an inner surface 19 of the base 2 so as to resiliently urge the latch in a direction which is away from said inner surface portion. As will be explained in more detail below, this is to retain the cover 3 in a clamped condition.

Figure 3:
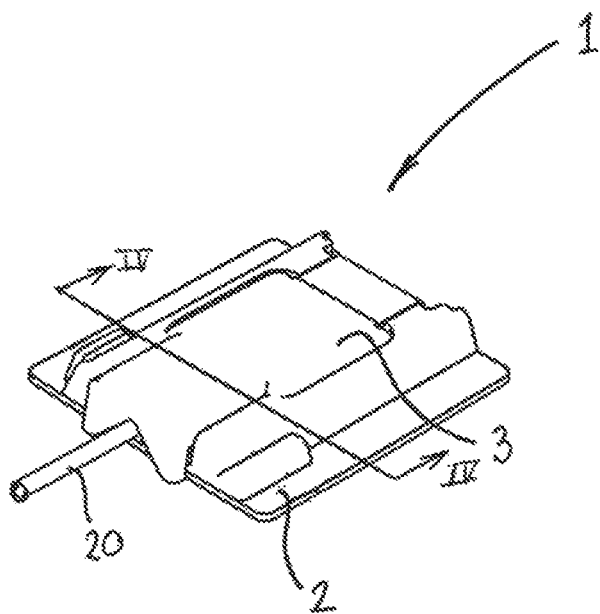
FIG. 3 is a perspective view of a catheter clamp in a closed condition.
Figure 4:
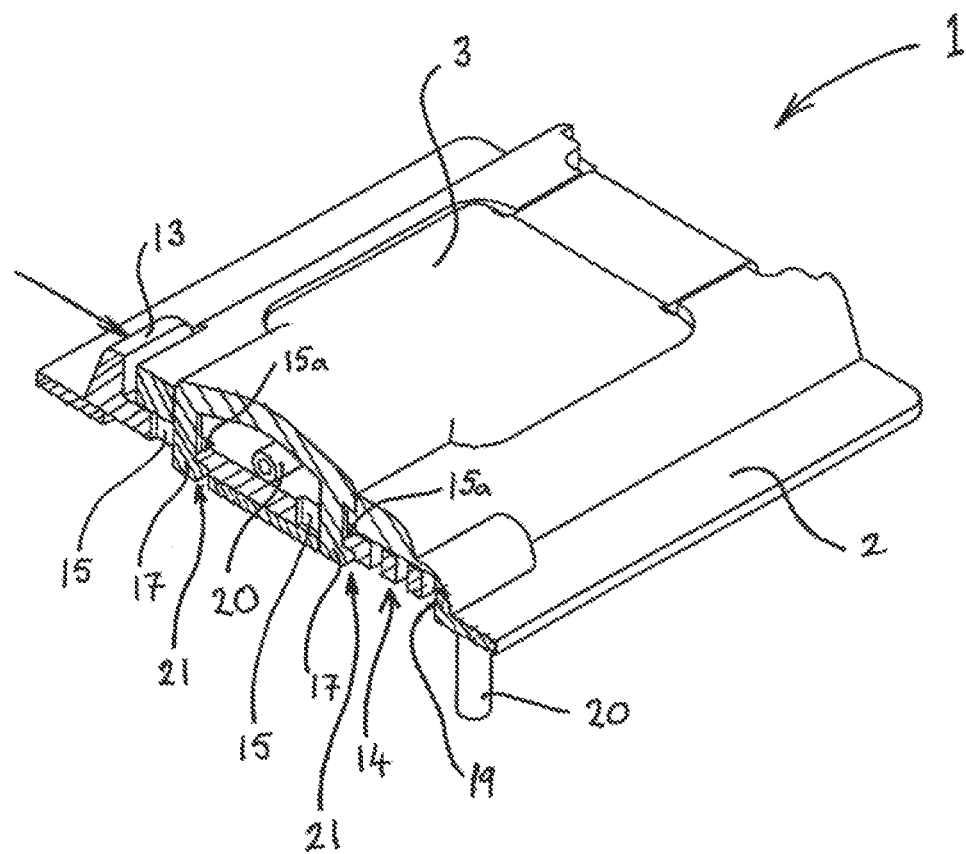
FIG. 4 is a perspective view on section IV-IV.
Figure 5:
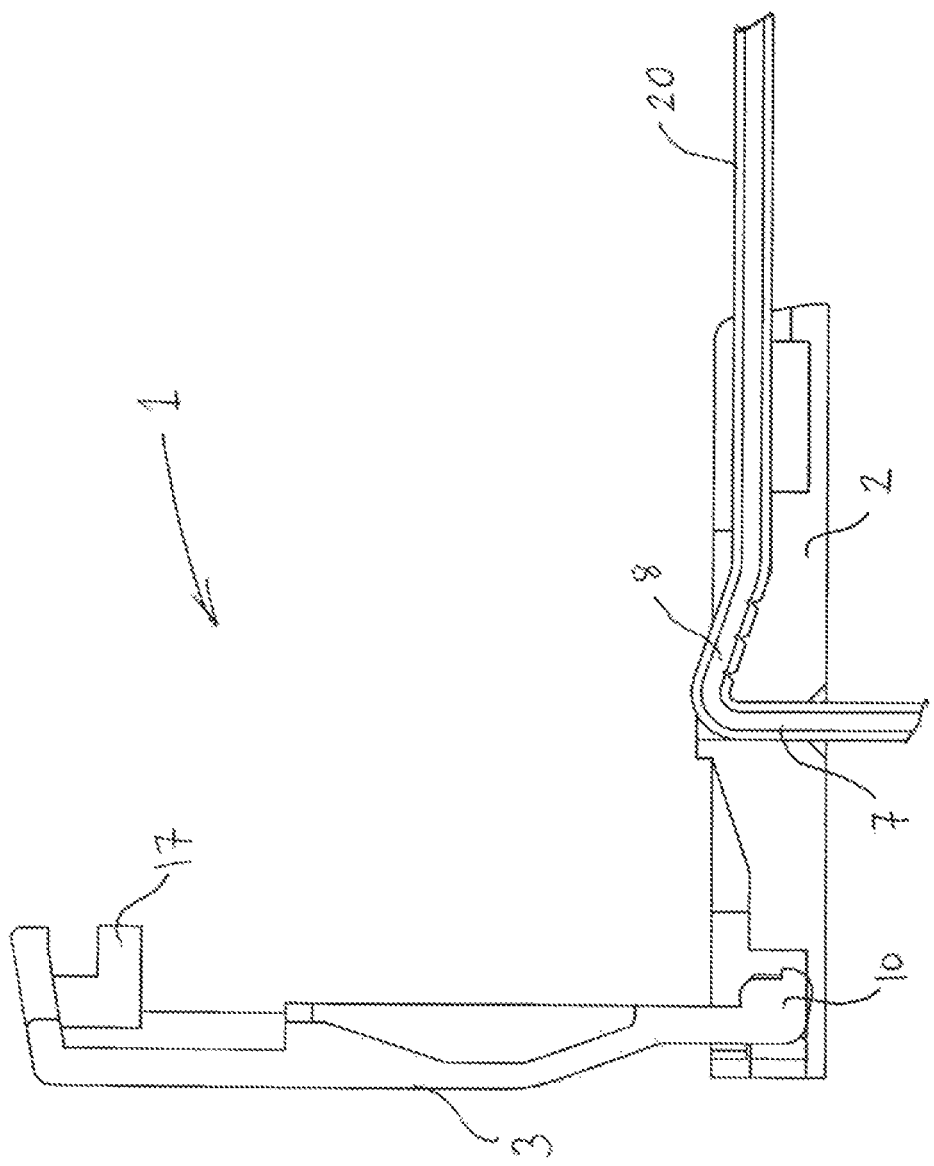
FIG. 5 is a view of longitudinal section of the catheter clamp in an open condition.

Reference is now made to FIGS. 3 and 4, which show the catheter clamp 1 in a clamped condition. With reference in particular to FIG. 4, it can be seen at the areas designated 21 that the retainer formations 17 are received in the apertures 15, and are retained by virtue of cooperation with respective lowermost surfaces of complimentary retainer formations 15a of the latch 12.

Figure 6:
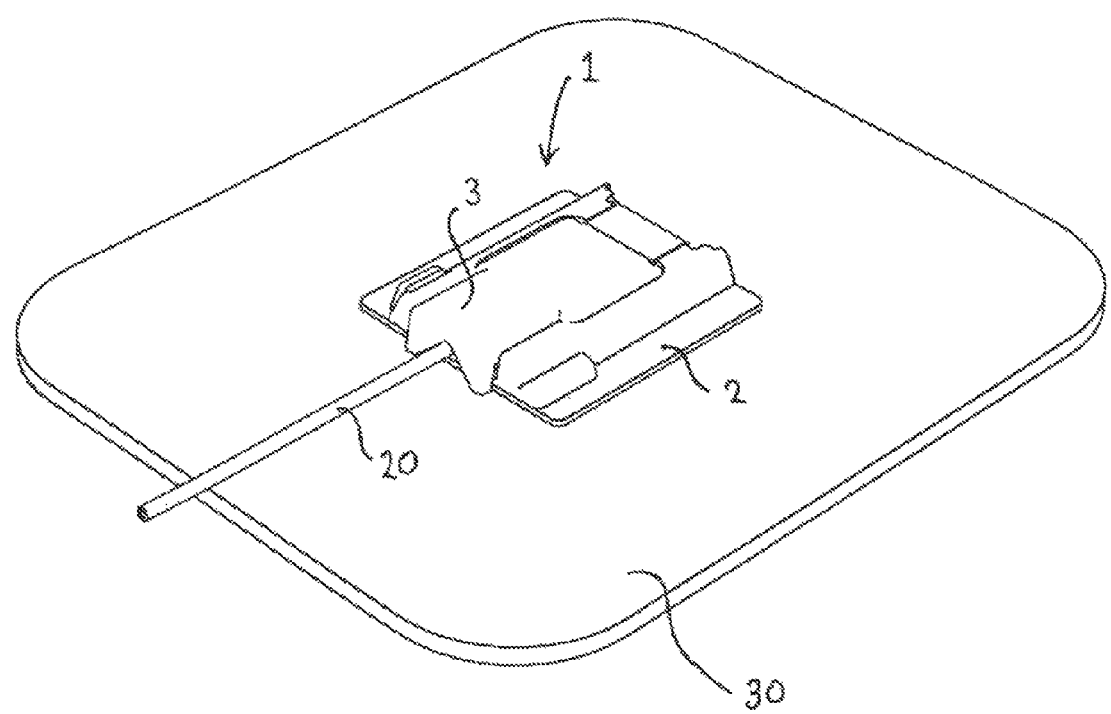
FIG. 6 is a perspective view of the catheter clamp in a clamped condition on an adhesive base pad.

With the catheter correctly located in the catheter clamp 1, in order for the cover 3 to adopt the clamped condition, a user pivots the cover 3 downwardly. On reaching the latch 12, inclined cam surfaces 17a of the retainer formations 17 bear against complimentary inclined cam surfaces 15a of the latch 12. As the user urges the cover 3 downwardly, engagement between the cam surfaces displaces the latch 12 laterally and so compresses the spring formation 14. In so doing, the retainer formations 17 are able to negotiate the retainer formations 15a of the latch and move downwardly through respective apertures 15. Having passed the retainer formations 15a, the compressed spring formation 14 forces the latch 12 to slide to return to a neutral position. In so doing the lowermost surfaces of the retainer formations 15a locate above retainer formations 17 and so maintain the cover 3 in the clamped condition. FIG. 6 shows the catheter clamp 1 in use in a clamped condition attached to an adhesive pad 30 (which is affixed to a patient's skin).

In order to open the cover, a user uses a finger to bear against the release portion 13 and urges it in the direction shown by the arrow in FIG. 4. This causes the retainer formations 15a out of vertical alignment with respective retainer formations 17. This in turn frees the cover 3 to be pivoted upwardly and out of the clamped condition and into the open condition. The cover is configured such that in the clamped condition a degree of flexure of the cover 3 is achieved such that the cover experiences a force which acts to urge the cover towards the open condition. Therefore, when the user slides the latch 12 to release the cover from the clamped condition, the cover will, as soon as the latch is released, 'spring' upwardly towards the open condition. It will be appreciated that because this release force acts perpendicularly to the direction of force required to operate the latch 12, advantageously the extent of engagement between the retainer formations of the cover and the latch does not affect the level of release/retain force, such that the extent of such engagement is sufficient to ensure that the cover would not be released without displacement of the latch.

A further advantage of the catheter clamp 1 is that the retainer formations 17 cannot be retained individually. Unless both lugs have fully passed through the apertures 15, the latch is unable to slide back so as to retain the cover in the clamped condition. Therefore, partial engagement of the retainer formations 17, and the consequential loss of grip of the catheter cannot occur.

The invention claimed is:

1. A catheter clamp comprising a base and a pivotable cover, the cover arranged to be capable of adopting an open condition and a clamped condition, the clamp further comprising a resiliently biased displaceable latch to releasably retain the cover in the clamped condition,
wherein the latch is carried on, and supported by, a support surface of the base in both the open condition and the clamped condition; and
wherein the latch is slidably displaceable on and relative to the support surface so as to release the cover from the clamped condition.

2. The catheter clamp of claim 1, wherein the latch is displaceably mounted in the base.

3. The catheter clamp of claim 1, wherein the cover comprises a retainer formation arranged to engage with the latch and retain the cover in a clamped condition.

4. The catheter clamp of claim 3, wherein the retainer formation depends from the cover.

5. The catheter clamp of claim 3, wherein the retainer formation is located towards a free end of the cover.

6. The catheter clamp of claim 3, wherein two spaced-apart retainer formations are provided.

7. The catheter clamp of claim 3, wherein the latch is provided with an aperture arranged to receive the retainer formation.

8. The catheter clamp of claim 3, wherein the retainer formation and the latch are provided with respective cam surfaces to facilitate displacement of the latch when urging the cover towards the clamped condition.

9. The catheter clamp of claim 8, wherein the cam surfaces are inclined.

10. The catheter clamp of claim 8, wherein the latch comprises a spring to provide resilient biasing towards retaining the cover in the clamped condition.

11. The catheter clamp of claim 1, wherein a clamping motive force maintains the cover in the clamped condition, and wherein the latch is slidable to allow the cover to be removed from the clamped condition in a direction which is substantially perpendicular to the direction of the clamping motive force.

12. The catheter clamp of claim 1, wherein the latch is slidable in a direction which is substantially parallel to an axis of the pivot of the cover.

13. The catheter clamp of claim 1, wherein the latch comprises a release portion to enable a user to slidably displace the latch.

14. The catheter clamp of claim 1, wherein the cover includes a structure, depending therefrom, with which the latch interacts to alternately retain the cover in the clamped condition or release the cover to the open condition.

15. The catheter clamp of claim 14, wherein the structure depending from the cover is a hook-shaped lug.

16. The catheter clamp of claim 1, wherein clamp is adapted for use on an area of human skin, and wherein the support surface faces upward, away from the area of human skin.

17. The catheter clamp of claim 1, wherein the latch is separate from both the base and the cover.

18. A catheter clamp comprising a base and a pivotable cover, the cover arranged to be capable of adopting an open condition and a clamped condition, the clamp further comprising a resiliently biased displaceable latch to releasably retain the cover in the clamped condition,
 wherein the latch is carried on, and supported by, a support surface of the base;
 wherein the latch is displaceable on and relative to the support surface so as to release the cover from the clamped condition; and
 wherein the base includes a vertical through-hole/bore and an open channel for receiving a catheter formed therein, the open channel being in communication with the through-hole/bore and extending along the base.

19. A clamp for a tubular medical article, comprising:
 a horizontal base having a support surface, a vertical through-hole/bore and an open channel, the open channel extending along the base and being in communication with the through-hole/bore;
 a pivotable cover, arranged to be capable of adopting an open condition and a clamped condition; and
 a resiliently biased displaceable latch that is carried on and supported by the support surface of the base in both the open condition and the clamped condition;
 wherein the latch may be slidably displaced, on and relative to the support surface, so as to releasably retain the cover in the clamped condition.

20. The clamp of claim 19, wherein a tubular medical article is extends along the base, through the open channel, and then downward through the vertical through-hole/bore.

* * * * *